United States Patent [19]

Moll et al.

[11] 4,165,643

[45] Aug. 28, 1979

[54] PROCESS AND APPARATUS FOR AUTOMATICALLY TAKING SAMPLES OF BEER FOR ANALYSIS

[75] Inventors: Manfred Moll, Richardmenil; Jean J. Delorme, Nancy; Jean C. Weber, Vandoeuvre, all of France

[73] Assignee: Tepral, France

[21] Appl. No.: 835,787

[22] Filed: Sep. 22, 1977

[30] Foreign Application Priority Data

Feb. 2, 1977 [FR] France .................................. 77 04025

[51] Int. Cl.$^2$ .............................................. G01N 1/16
[52] U.S. Cl. .................................................. 73/421 B
[58] Field of Search ............... 73/421 B; 195/103.5 R; 204/195 R, 195 B

[56] References Cited

U.S. PATENT DOCUMENTS

| | | | |
|---|---|---|---|
| 2,082,299 | 6/1937 | Nonhebel et al. | 73/421 B |
| 2,348,806 | 5/1944 | Gillard et al. | 73/421 B |
| 2,675,706 | 4/1954 | Edgar | 73/421 B |
| 3,369,405 | 2/1968 | Galegar | 73/421 B |

Primary Examiner—S. Clement Swisher
Attorney, Agent, or Firm—Robert E. Burns; Emmanuel J. Lobato; Bruce L. Adams

[57] ABSTRACT

This invention relates to a process for the automatic representative taking of samples of fermented beverages. The method consists in taking samples at several different points in height of the fermentation tank, cooling them and proceeding with a determination of the cells in suspension, measuring the hydrogen potential, the dissolved oxygen, the temperature, and the conductivity, carrying out a chromatographic analysis of the volatile and other matters in accordance with a sequence which depends on the state of advance of the fermentation, and is carried out by an automatic device. The installation is characterized by the fact that it comprises a principal conduit having a water inlet at its end and to which there are connected various sampling conduits, it continues into the exchanger of a refrigerating group and is connected to a measurement unit which has a fluid wiredrawing device at its end. The invention applies to the fermented liquid fermentation industry.

9 Claims, 3 Drawing Figures

PROCESS AND APPARATUS FOR AUTOMATICALLY TAKING SAMPLES OF BEER FOR ANALYSIS

This invention relates to a process and installation intended to be used for the automatic representative obtaining of samples of beer in the course of fermentation in a fermentation tank of large volume in order to obtain control measurements.

For many years, high-volume fermentation tanks located outdoors have been used in which there are fermented and simultaneously stored large quantities of beer on the order of 10,000 hectoliters.

Of course, this enormous quantity of wort requires careful supervision and in the course of its fermentation samples which are deemed representative are periodically taken and analyzed in detail.

One parameter or another of the fermenting beer is modified on basis of these results.

Unfortunately, practically all of the sampling and analysis operations are carried out manually, bringing about irregularity in measurement due to excessive time intervals between the measurements and making it necessary for the supervisory and analytical personnel to follow up—unfortunately in too imprecise a manner—the course of the fermentation.

Furthermore, the formation of foam at the time of the taking of the sample disturbs the measurements.

The object of the invention is to sample and automatically analyze a liquid which is charged with gas in a high-capacity tank, particularly beer, during the course of fermentation from its fermentation tank by a representative sample so as to increase the frequency, number, and reliability of the measurements.

For this purpose, the invention is characterized by an apparatus composed of a principal conduit connected to a source of water and to which there are connected by means of solenoid valves a plurality of sampling conduits arranged over the entire height of the fermentation tank, the conduit continuing into a refrigeration heat exchanger connected by a section having a sampling valve and connected to a measurement unit which is protected against the formation of foam by a fluid wiredrawing device and the cold.

This invention has a large number of advantages, namely:

it makes it possible to carry out the measurements of the different parameters of the fermenting beer while avoiding any disturbance or error due to the formation of foam which is inevitable in the case of manual sampling.

only the minimum amount of beer necessary for the measurements is used due to the use of water in order to push the sample of beer into the conduits and into the measurement members.

its operation is entirely automatic by means of an automatic device which acts indirectly on the solenoid valves which are located at each branching point, making it possible to isolate the circuits as desired.

furthermore, it is possible to recover the beer which has been used for the measurements and to recycle it, for instance, to a hopping boiler in order to avoid any infection.

due to its automatic operation, it becomes possible to adjust the frequency of the samplings as a function of the state of advance of the fermentation and thus to decrease those losses in beer which are due to the necessity of periodic analyses.

increase in the frequency and number of measurements without any human action.

The invention will be better understood from a reading of the following description which is given by way of illustration and not of limitation, in conjunction with the drawings in which.

Figure 1:
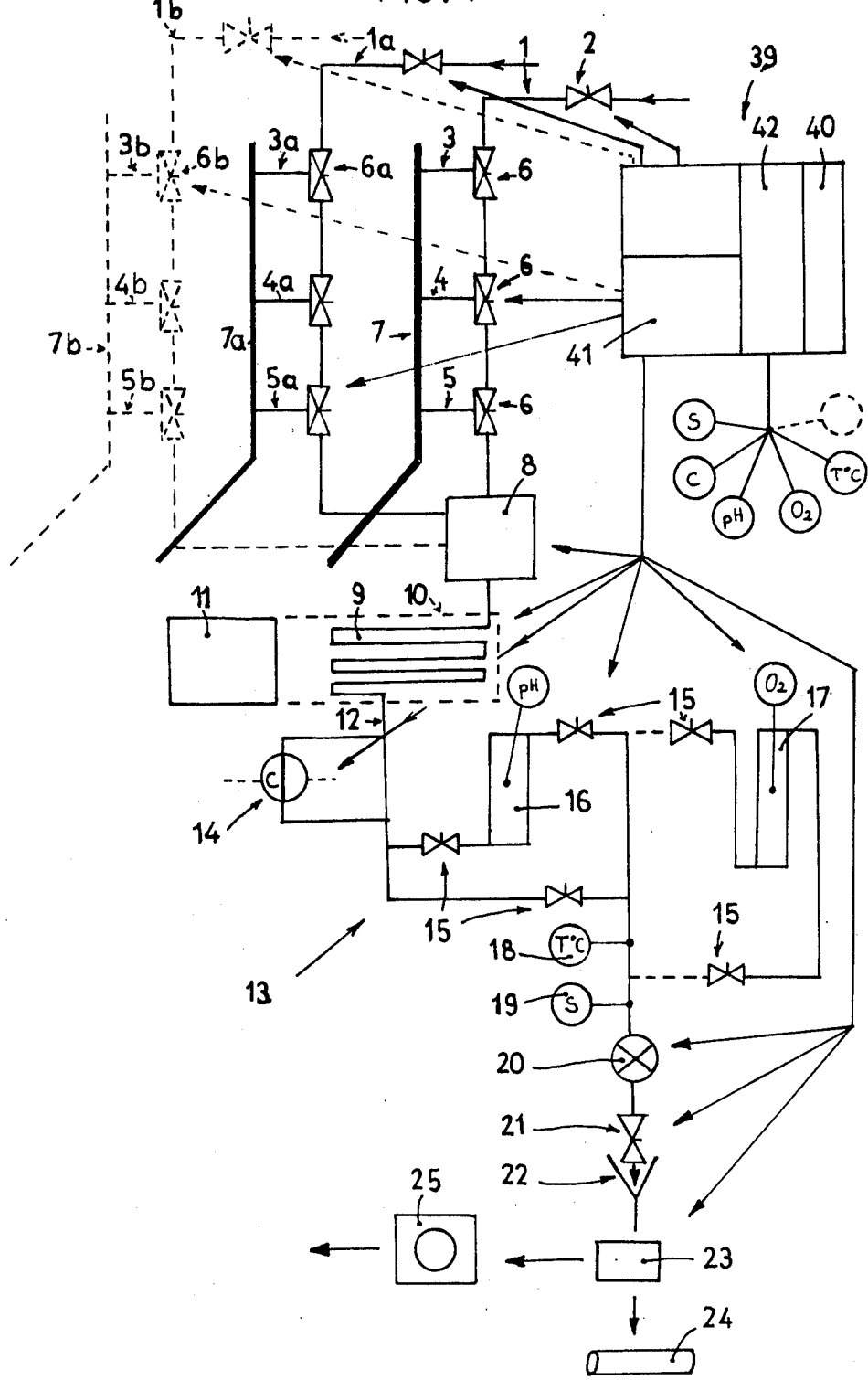
FIG. 1 is a diagram of the installation without gaseous-phase chromatographic measurement.

The installation is in the form of two variants one of which combines the measurements in a measurement enclosure and includes a chromatographic analysis while the other provides only separate analyses.

The installation is composed of a principal sampling conduit 1 which is provided at its upper end with a water inlet through an inlet solenoid valve 2; from this conduit there branch off a plurality of sampling conduits, for instance three conduits 3, 4, 5 through three-way solenoid valves such as 6, 6a, 6b arranged along the height of the fermentation tank 7.

The principal conduit leads to a solenoid valve or to a multiway regrouping unit 8 to which there are connected similar principal conduits 1a, 1b etc. connected to other fermentation tanks 7a, 7b, etc. for successive sequential samplings in the case of a centralized fermentation conduit which covers a unit comprising a plurality of tanks.

The principal conduit 1 extends from the unit 8 to a coil 9 in the heat exchanger 10 of a refrigerating group 11, which is for instance independent, and then emerges through a section 12 which is connected to a measurement unit 13 which comprises a measuring station at which there is mounted a bypass circuit containing a sampling valve 14 for sampling and determination of the cells in suspension, indicated by C.

It may be pointed out that the refrigeration group is in principle independent, but the heat exchanger may utilize the cold-producing fluid which is intended to cool the fermentation tank.

In a first embodiment (FIG. 1) without gaseous-phase chromatographic measurement, the measurement assembly 13 comprises, isolated by valves 15 and mounted in parallel, measurement cells including a probe 16 for measuring the hydrogen potential labeled pH, a probe 17 for measuring the dissolved oxygen, labeled $O_2$ and, in series, a probe 18 for measuring the temperature, labeled T°C. and a probe 19 for determining the conductivity of the liquid, labeled S.

The valves 15 assure suitable isolation of the measurement cells for their maintenance, in particular their cleaning.

This measurement assembly 13 furthermore comprises at its end a fluid wiredrawing device 20 of adjustable cross section mounted at the end of the circuit in front of an outlet solenoid valve 21 discharging into a collector 22 which feeds a distributor 23 for evacuating the water towards the sewer 24 and evacuating the samples of beers towards a hopping boiler 25 for the recycling thereof without danger of infection.

Figure 3:
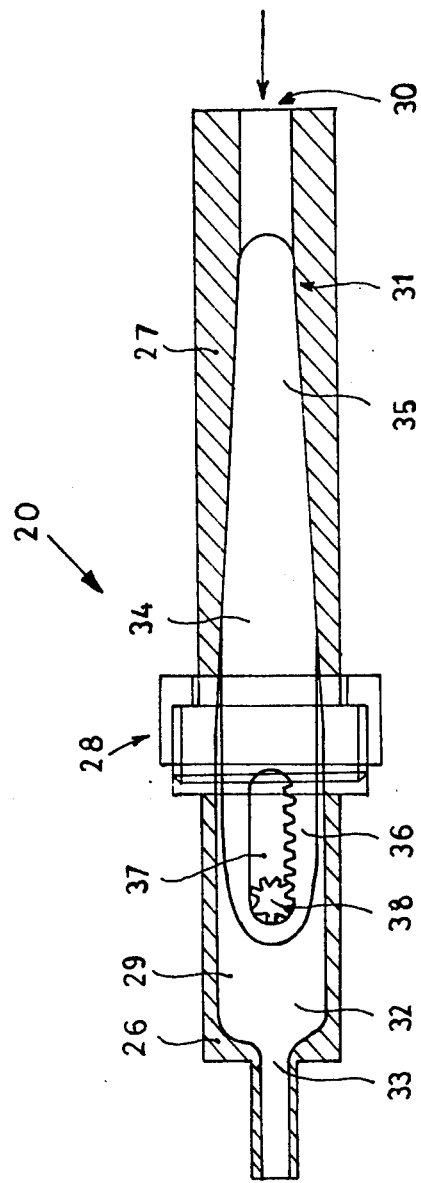
FIG. 3 is a basic diagram in longitudinal section of the fluid wiredrawing device.

The fluid wiredrawing device 20 is shown in FIG. 3 and comprises in general a cylindrical section composed of two complementary parts 26 and 27 which are connected together by overlap and held together by fastening means 28. In its interior it has a cavity 29 of adjustable section provided, in the direction from upstream to downstream with an inlet 30 opening onto a divergent nozzle cone 31 which opens into a turbulence chamber 32 with progressive outlet neck 33 of gentle curvature. This section is inserted in the circuit at the end of the measurement unit 13 in front of the outlet solenoid valve 21 or, by way of exception, in front of the measurement unit.

The inner cavity 29 contains a movable profiled piston 34 of ovoidal longitudinal section which is actuated to undergo longitudinal displacement so as to vary the cross section of passage of the fluid.

The piston is formed of a rear portion 31 which is greatly elongated and has a profile which is complementary to that of the nozzle 31. The body of this system has, at its front portion 36, an ovoid extension with rounded front surface having a central opening 37 provided with displacement means. These means are developed, for instance, in the form of a rack associated with a worm gear 38 driven from the outside by a suitable device.

Thus the movement of displacement in the direction of advance of the fluid frees the rear part 35 of this body from thw walls of the nozzle 31 and increases the space between it and its shell while its front portion 36 approaches the neck 33.

This combined effect makes it possible, while increasing the cross section of passage, to reduce to a minimum the formation of foam, thus favoring a progressive flow. Conversely, movement in the opposite direction causes a constriction at the upstream portion of the cavity.

The operation of the assembly is assured with respect to drive and coordination by a multichannel automatic device 39.

Its role consists in controlling the sampling sequences for one and the same tank and interposing during the time of non-supervision of said tank the sampling sequences of one or more other tanks.

It comprises a programmable unit 40 and control circuits 41 for the picking up and transmission of the measurements and the signals from the pick-up unit 42 which has different pick-ups connected to respective ones of the probes of the measurement unit 13.

Figure 2:
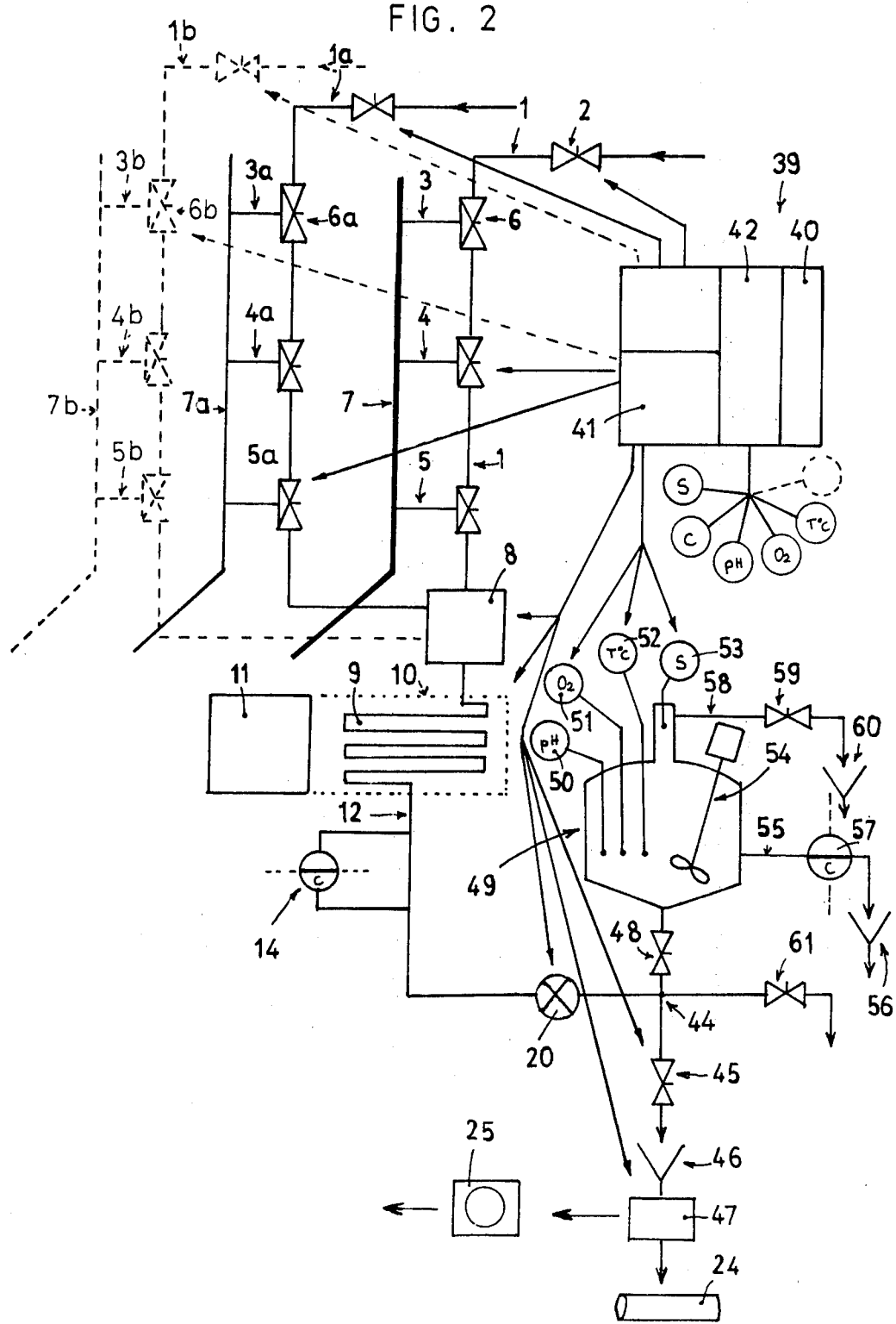
FIG. 2 is a diagram of the installation with gaseous-phase chromatographic measurement.

The second embodiment (FIG. 2) which has chromatographic measurement, is provided with a different measurement assembly 43 having the fluid wiredrawing device 20 with adjustable discharge located preferably upstream and having the same sampling valve 14 as the measurement assembly 13, as well as various other common members.

In this case, the principal conduit 1 is continued by a branch 44, a solenoid valve 45 controlling the emergence of the sampled liquid and the surplus water towards the outside via a collector 46 which feeds the distributor 47 for evacuation to the sewer 24 in the case of the water or to the hopping boiler 25 in the case of the samples.

At the location of the branching 24 there is provided the measurement branch which consists of a solenoid valve 48 and a measurement enclosure 49 in which there are combined all of the measurements by probes such as the probe 50 for the measurement of the hydrogen potential, labeled pH, the probe 51 for the measurement of the amount of dissolved oxygen, labeled $O_2$, the probe 52 for measuring the temperature labeled T°C., a probe 53 for measuring the conductivity, labeled S, and having an agitator 54 provided within the enclosure 49 to homogenize the liquid and unclog the probes.

The measurement enclosure 49 furthermore comprises a side outlet 55 towards which discharges to a second collector 56 through a sampling valve 57, and an upper outlet 58 connected to a purge solenoid valve 59, which places the receptacle under air and, at its other outlet, effects a discharge of the liquid through a third collector 60.

At the location of the branching 44, there is also attached the branch which feeds the chromatographic analysis circuit via a solenoid valve 61.

The automatic device 39 described diagrammatically above is used in this second variant with certain evident adaptations.

The different operating phases of the installation in accordance with the invention will be described below, particularly the sequence of the sampling. The system operates entirely automatically and the different commands come from the automatic device 39 which controls the sampling sequence or sequences.

The circuit is filled with water and the fluid wiredrawing device such as 20, located at the end of the circuit, is enclosed at the beginning of the sequence. When the sampling command is given, the fermentation tank, via a sampling conduit, is placed in contact with the circuit by an open solenoid valve and the device opens. The beer gradually fills the circuit pushing out the water. The conductivity probe located at the end of the circuit detects the moment when the circuit is full of beer and the possible formation of foam and transmits this information to the automatic device 39 which orders the closing of the solenoid valve, placing the system in contact with the tank.

The beer remains in the circuit and the different measurements are carried out. In order to decrease the amount of beer withdrawn, the beer is pushed by water which therefore occupies the principal transfer conduit during the measurements.

This is followed by a rinsing sequence and a new filling with water.

In order to assure the representative nature of the sample, a certain amount of beer is rejected before the measurements are effected. For this purpose, the wiredrawing device closes and the beer stays in the circuit for the time necessary to effect the different measurements. The circuit is then rinsed with water and is again in its initial state.

The sampling process in accordance with the invention for the analysis of the principal parameters will now be described.

Use is made of the combined effects of coldness and the decrease of the sudden pressure surges as a result of the presence of the fluid wiredrawing device. The cold increases the solubility of the carbon dioxide and pressure changes favor the formation of foam.

One therefore has conditions making it possible to reduce the formation of foam to a minimum and even to prevent it.

One proceeds by samplings in accordance with an automatic succession of sequences in at least three points over the entire height of one or more fermentation tanks successively. The principal conduit or conduits is driven with water at the start and the principal conduit connected to the tank to be supervised is placed in communication with the cooling and measurement assembly; the different solenoid valves of the secondary conduits are opened successively in accordance with a sequence specific to each fermentation tank, the circuit is left under water load before and after the passage of the sample, the liquid sample is cooled uniformly within the range of 0° to 5° C. and preferably between 0° and 2° C., one makes certain of the passage of the sample and of the total absence of foam before analysis by a conductivity measurement; a determination of the cells in suspension, the measurements of the hydrogen potential, of the dissolved oxygen, of the temperature and also a chromatographic analysis of the volatile substances are carried out in the same measurement enclosure or in series.

It will be noted that in each measurement sequence, the amount of sample taken is reduced to the minimum amount strictly necessary by pushing the sample through the measurement unit with water.

The measurement assembly is rinsed with water before going over to a new sequence.

At the end of the cycle and the circuit one effects, through a three-way valve, the discharge of the quantity of driving and rinsing water and the recovery of the samples of beer taken after treatment in a hopping boiler.

The invention has been described in detail but it is obvious that the embodiments which derive therefrom by the use of equivalent means, simple modifications or partial substitutions also fall within its scope.

We claim:

1. A process for sampling and measuring beer fermentation products stored within a fermentation tank comprising the steps of: providing a main sampling conduit having branch conduits each connected to the fermentation tank at different vertical locations for sampling therefrom beer fermentation products; initially charging said main sampling conduit with water; withdrawing a sample of beer fermentation products through one branch conduit at a time into the main sampling conduit while maintaining the other branch conduits isolated from the main sampling conduit; advancing the withdrawn sample of beer fermentation products through the main sampling conduit to a measurement station by pushing it with water to thereby minimize the amount of beer fermentation products withdrawn from the fermentation tank for sampling and measuring purposes; and measuring certain properties of the withdrawn sample at the measurement station and providing corresponding output signals each representative of a measured property of the beer fermentation products at the particular vertical location of the fermentation tank at which the measured sample was withdrawn.

2. A process according to claim 1; including rinsing the main sampling conduit with water between successive withdrawing steps.

3. A process according to claim 1; including automatically carrying out the withdrawing, advancing and measuring steps in a predetermined sequence according to a predetermined program.

4. A process according to claim 1; including setting the temperature of the withdrawn sample between 0° and 5° C. before carrying out said measuring step so as to minimize the presence of foam in the withdrawn sample to thereby reduce errors in the measurements which would otherwise be introduced due to foam.

5. A process according to claim 4; wherein the temperature of the withdrawn sample is set between 0° and 2° C.

6. A process according to claim 1; wherein said measuring step comprises measuring at least one of the properties of temperature, dissolved oxygen, hydrogen potential and electrical conductivity of the withdrawn sample.

7. A process according to claim 1; wherein said measuring step comprises measuring the properties of temperature, dissolved oxygen, hydrogen potential and electrical conductivity of the withdrawn sample.

8. A process according to claim 1; including agitating the withdrawn sample at the measurement station and withdrawing any foam which may be formed during agitation preparatory to carrying out said measuring step.

9. A process according to claim 1; wherein said advancing step comprises controlling the flow of the withdrawn sample to the measurement station by progressively and gradually increasing the cross-section of the flow passage to reduce to a minimum the formation of foam.

* * * * *